United States Patent
Timken

(10) Patent No.: US 8,728,301 B2
(45) Date of Patent: May 20, 2014

(54) INTEGRATED BUTANE ISOMERIZATION AND IONIC LIQUID CATALYZED ALKYLATION PROCESSES

(75) Inventor: Hye Kyung Cho Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 130 days.

(21) Appl. No.: 13/230,757

(22) Filed: Sep. 12, 2011

(65) Prior Publication Data

US 2013/0062253 A1    Mar. 14, 2013

(51) Int. Cl.
| | | |
|---|---|---|
| *C10G 65/00* | (2006.01) | |
| *C10G 65/02* | (2006.01) | |
| *C10G 65/04* | (2006.01) | |
| *C10G 45/60* | (2006.01) | |
| *C10G 35/06* | (2006.01) | |

(52) U.S. Cl.
USPC .............. 208/64; 208/49; 208/133; 208/134; 208/135; 208/141; 585/331; 585/332; 585/734; 585/706

(58) Field of Classification Search
USPC .............. 208/46, 133, 134, 135, 141, 49, 64; 585/331, 332, 734, 709
See application file for complete search history.

(56) References Cited

U.S. PATENT DOCUMENTS

| | | | |
|---|---|---|---|
| 7,432,408 B2 | 10/2008 | Timken et al. | |
| 7,439,410 B1 * | 10/2008 | Rice et al. | ..................... 585/332 |
| 7,572,943 B2 | 8/2009 | Elomari et al. | |

OTHER PUBLICATIONS

Chauvin, Y, et al., Alkylation of isobutane with 2-butene using 1-butyl-3-methylimidazolium chloride-aluminum chloride molten salts as catalysts, Journal of Molecular Catalysis, 1994, Elsevier, vol. 92, pp. 155-165.*
Perry's Chemical Engineer's Handbook, 2008, 8th Ed., McGraw-Hill, pp. 8-44.*

* cited by examiner

*Primary Examiner* — Walter D Griffin
*Assistant Examiner* — Derek Mueller
(74) *Attorney, Agent, or Firm* — Steven H. Roth

(57) ABSTRACT

Integrated isomerization and ionic liquid catalyzed alkylation processes may comprise integrating ionic liquid alkylation and n-butane isomerization using a common distillation unit for separating an n-butane containing fraction from at least one of an alkylation hydrocarbon phase from an ionic liquid alkylation reactor and an isomerization hydrocarbon stream from an isomerization unit. The n-butane containing fraction may undergo isomerization to provide an isomerization reactor effluent comprising the isomerization hydrocarbon stream. An isobutane containing fraction, separated from at least one of the alkylation hydrocarbon phase and the isomerization hydrocarbon stream, may be recycled from the distillation unit to the ionic liquid alkylation reactor.

20 Claims, 4 Drawing Sheets

INTEGRATED BUTANE ISOMERIZATION AND IONIC LIQUID CATALYZED ALKYLATION PROCESSES

TECHNICAL FIELD

The present invention relates to integrated butane isomerization and ionic liquid catalyzed alkylation processes.

BACKGROUND

Conventional paraffin-olefin alkylation plants may be used in conjunction with a conventional n-butane isomerization plant in order to provide additional feedstock (isoparaffin) for the alkylation plant. Conventional n-butane isomerization processes use $AlCl_3$ catalyst or a Pt-alumina catalyst plus HCl. Since the isomerization catalyst is sensitive to moisture, conventional n-butane isomerization processes require extensive feed drying.

Hydrofluoric acid (HF) is used as a catalyst in conventional alkylation processes for the production of high-octane gasoline, distillate, and lubricating base oil. The hazards of HF, e.g., related to HF volatility, are well documented. The use of additives to reduce HF volatility is expensive and does not eliminate the need for large quantities of HF in the plant. Efforts to develop safer, alternative catalysts have encountered serious challenges. The conversion of HF alkylation units to use sulfuric acid ($H_2SO_4$) as catalyst requires significant added capital and operating expense, and at the same time introduces the hazards associated with highly corrosive concentrated $H_2SO_4$. Further, solid alkylation catalysts have proved difficult to commercialize due to rapid fouling and deactivation. The quest for alternative catalytic systems to replace conventional HF and $H_2SO_4$ catalysts in alkylation processes has been researched by various groups in both academic and industrial institutions. Thus far, no alternative catalyst for performing such processes has been commercialized.

Recently there has been considerable interest in metal halide ionic liquid catalysts as alternatives to HF and $H_2SO_4$ catalysts. As an example, the ionic liquid catalyzed alkylation of isoparaffins with olefins is disclosed in U.S. Pat. No. 7,432,408 to Timken, et al. Further, U.S. Pat. No. 7,572,943 to Elomari, et al. discloses the ionic liquid catalyzed oligomerization of olefins and the alkylation of the resulting oligomers(s) with isoparaffins to produce alkylated olefin oligomers.

FIG. 1A schematically represents a conventional n-butane isomerization plant 10 according to the prior art. Conventional n-butane isomerization plant 10 includes a feed dryer 12, an isomerization reactor 14, a gas/liquid separation unit 16, a distillation unit 18, and a caustic (KOH or NaOH) treating unit 20. Dried n-butane or a mixed butane stream containing a significant amount of n-butane is co-fed with dried $H_2$ to isomerization reactor 14. The $H_2$ and HCl are removed from the reactor effluent via gas/liquid separation unit 16. The resultant hydrocarbon effluent (isomerized butane mixture) is sent to distillation unit 18 to separate n-butane from the isobutane product. The isobutane stream is treated in caustic treating unit 20 to remove residual chloride in the isobutane product stream before being sent to a conventional HF or $H_2SO_4$ alkylation plant (see, e.g., FIGS. 1B and 1C).

FIG. 1B schematically represents a conventional HF alkylation plant 30, in relation to a conventional butane isomerization plant, according to the prior art. HF alkylation plant 30 may include a feed treatment unit 32, an HF alkylation reactor 34, an HF settler 36, an HF heat exchanger 38, an HF regeneration unit 40, a fractionation unit 42, and a product treatment unit 44. An olefin containing stream is fed to HF reactor 34 together with an isobutane containing stream from a conventional butane isomerization plant (see, e.g., FIG. 1A). The effluent from HF reactor 34 is separated via HF settler 36 into a hydrocarbon phase and an HF phase. The HF phase is recycled to HF reactor 34 via HF heat exchanger 38. The hydrocarbon phase is fractionated via fractionation unit 42, and one or more fractions treated via product treatment unit 44 to provide one or more products.

FIG. 1C schematically represents a conventional $H_2SO_4$ alkylation unit 30', in relation to a conventional butane isomerization plant, also according to the prior art. $H_2SO_4$ alkylation plant 30' may include an $H_2SO_4$ alkylation reactor 34', an acid settler 36', an acid wash vessel 24, an alkaline water wash vessel 26, a refrigeration unit 28, a fractionation unit 42', and a product treatment unit 44'. An olefin containing stream is fed to $H_2SO_4$ reactor 34' together with an isobutane containing stream from a conventional butane isomerization plant (see, e.g., FIG. 1A). The effluent from $H_2SO_4$ reactor 34' is separated via acid settler 36' into a hydrocarbon phase and an acid phase. A portion of the acid phase is recycled to $H_2SO_4$ reactor 34'. A further portion of the acid phase may be removed for acid regeneration. Fractionation unit 42' fractionates the hydrocarbon phase to provide one or more products for treatment by product treatment unit 44'.

Conventional processes for both n-butane isomerization and HF/$H_2SO_4$ catalyzed alkylation are well known in the art.

U.S. Pat. No. 7,439,410 to Rice et al. discloses an integrated isomerization-alkylation process that uses a common distillation zone, in which the isomerization reaction zone effluent is passed to a depropanizer, either directly or via a chloride treater. In an alternative embodiment of the '410 patent, the isomerization reaction zone effluent is cooled and then undergoes gas-liquid phase separation before the liquid phase is passed to the depropanizer via the chloride treater. During alkylation according to the '410 patent, the reactants may be in the vapor-, liquid-, or mixed liquid-vapor phase when contacted with the catalyst particles.

There is a need for efficient, integrated ionic liquid catalyzed alkylation-butane isomerization processes.

SUMMARY

In an embodiment of the present invention there is provided an integrated ionic liquid alkylation and n-butane isomerization process comprising contacting at least one isoparaffin and at least one olefin with an ionic liquid catalyst in an ionic liquid alkylation zone under ionic liquid alkylation conditions; separating an alkylation hydrocarbon phase from an alkylation reactor effluent of the ionic liquid alkylation zone; fractionating, via a distillation unit, an internal hydrocarbon feed to provide an n-butane containing fraction, wherein the internal hydrocarbon feed comprises the alkylation hydrocarbon phase; isomerizing at least a portion of the n-butane in the n-butane containing fraction to provide isobutane; and recycling the isobutane to the ionic liquid alkylation zone.

In another embodiment, there is provided an integrated ionic liquid alkylation-butane isomerization process comprising contacting at least one isoparaffin and at least one olefin with an ionic liquid catalyst in an ionic liquid alkylation zone under ionic liquid alkylation conditions; separating an alkylation hydrocarbon phase from an alkylation reactor effluent of the ionic liquid alkylation zone; fractionating, via a distillation unit, an internal hydrocarbon feed to provide an n-butane containing fraction, wherein the internal hydrocarbon feed comprises the alkylation hydrocarbon phase; contacting the n-butane containing fraction with an isomerization catalyst in an isomerization zone under butane isomerization conditions; separating an isomerization reactor effluent of the isomerization zone into a gas phase and an isomerization hydrocarbon stream, wherein the isomerization hydrocarbon stream comprises isobutane, and the internal hydrocarbon feed further comprises the isomerization hydrocarbon stream; fractionating, via the distillation unit, the internal hydrocarbon feed to further provide an isobutane containing fraction; and recycling the isobutane containing fraction to the ionic liquid alkylation zone.

In a further embodiment, there is provided an integrated ionic liquid alkylation and n-butane isomerization process comprising contacting at least one isoparaffin and at least one olefin with an ionic liquid catalyst in an ionic liquid alkylation zone under ionic liquid alkylation conditions; separating an alkylation hydrocarbon phase from an alkylation reactor effluent of the ionic liquid alkylation zone; fractionating, via a distillation unit, an internal hydrocarbon feed to provide an n-butane containing fraction, wherein the internal hydrocarbon feed comprises the alkylation hydrocarbon phase and an isomerization hydrocarbon stream; contacting the n-butane containing fraction with an isomerization catalyst in an isomerization reactor under butane isomerization conditions to provide an isomerization reactor effluent comprising the isomerization hydrocarbon stream; separating the isomerization hydrocarbon stream from the isomerization reactor effluent; recycling the isomerization hydrocarbon stream to the distillation unit; separating, via the distillation unit, an isobutane containing fraction from the internal hydrocarbon feed; and recycling the isobutane containing fraction to the ionic liquid alkylation zone.

As used herein, the terms "comprising" and "comprises" mean the inclusion of named elements or steps that are identified following those terms, but not necessarily excluding other unnamed elements or steps.

DETAILED DESCRIPTION

Figure 1A:
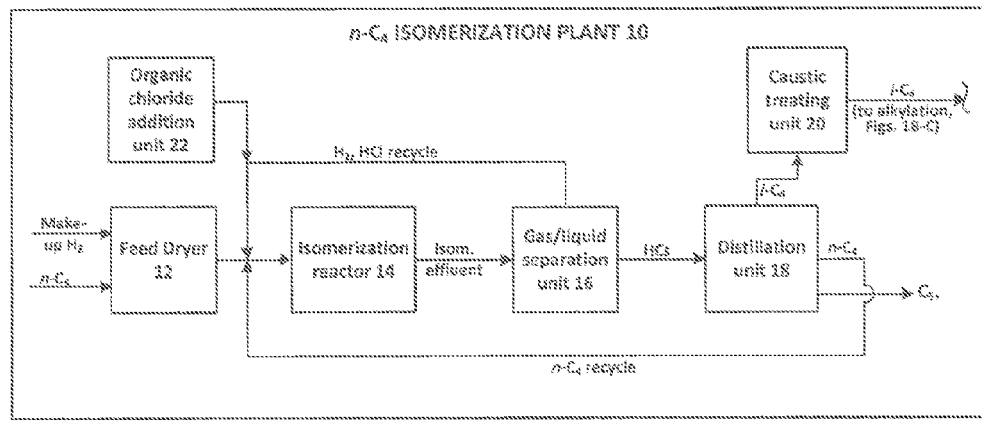
FIG. 1A schematically represents a conventional n-butane isomerization plant, in relation to a conventional HF or $H_2SO_4$ alkylation plant, according to the prior art.
Figure 1B:
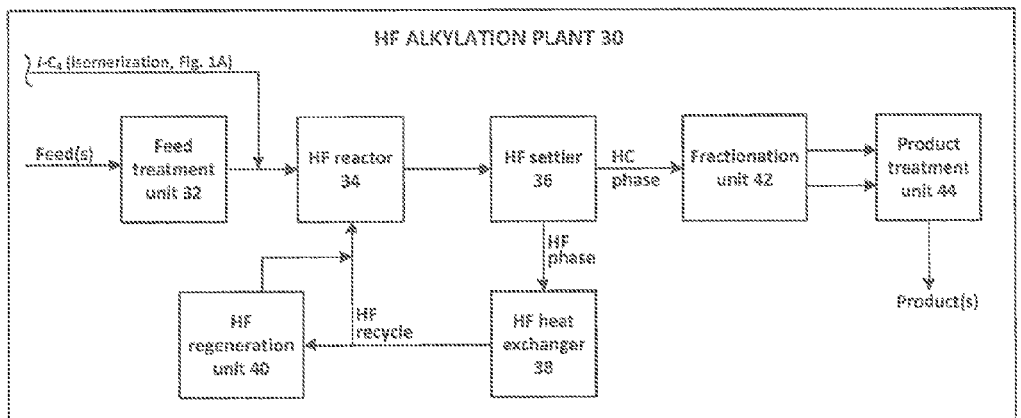
FIG. 1B schematically represents a conventional HF alkylation plant, in relation to a conventional n-butane isomerization plant, according to the prior art.
Figure 1C:
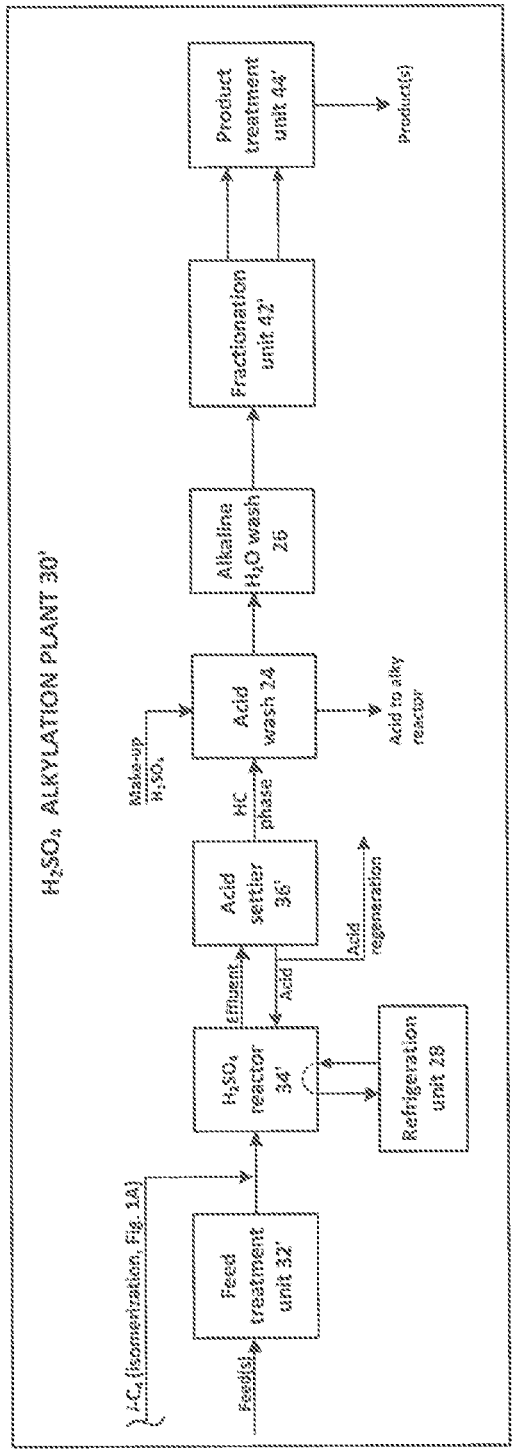
FIG. 1C schematically represents a conventional $H_2SO_4$ alkylation plant, in relation to a conventional n-butane isomerization plant, according to the prior art.

Ionic liquid catalysts may be useful for a range of hydrocarbon conversion reactions, including alkylation reactions for the production of alkylate gasoline blending components, distillate, lubricants, and the like. In an embodiment, the present invention provides processes that integrate ionic liquid catalyzed isoparaffin-olefin alkylation with n-butane isomerization.

Applicants have found that by integrating n-butane isomerization with ionic liquid catalyzed alkylation, the n-butane isomerization process, and/or the alkylation process, or the combination of these two processes, can be significantly simplified while providing substantial benefits. For example, integrated processes for ionic liquid catalyzed alkylation-butane isomerization, as disclosed herein, may not only increase the efficiency of alkylation, but also decrease capital expenditure and operating costs.

Apart from the avoidance of conventional $H_2SO_4$ and HF catalysts, integrated ionic liquid catalyzed alkylation-butane isomerization processes offer numerous additional advantages over prior art processes for alkylation and n-butane isomerization. Such advantages may include:

(1) Feed drying can be combined and simplified in the integrated ionic liquid alkylation-butane isomerization process. In ionic liquid catalyzed alkylation, the feeds to the ionic liquid alkylation reactor may be thoroughly dried such that, in the integrated process, the n-butane stream from the distillation unit to the isomerization reactor may not require further drying. Thus, the feed dryer for drying the n-butane feed to the isomerization reactor (in prior art processes) may be eliminated.

(2) The total number of distillation columns used for conventional alkylation and n-butane isomerization processes may be reduced by integrating ionic liquid catalyzed alkylation and n-butane isomerization. In integrated ionic liquid alkylation-butane isomerization processes, the hydrocarbon product from the n-butane isomerization unit can be sent to the shared distillation columns en masse together with the hydrocarbon phase from the ionic liquid alkylation reactor. By combining the distillation of hydrocarbon products from the ionic liquid alkylation and n-butane isomerization reactions, one or more costly distillation columns can be eliminated.

(3) A dedicated chloride addition unit, which is used to feed make-up organic chloride (e.g., $CCl_4$ or $CHCl_3$) to the isomerization reactor in prior art processes, can be eliminated or omitted. In ionic liquid catalyzed alkylation, an HCl containing fraction derived from the alkylation reactor effluent can be fed to the isomerization reactor, in lieu of the addition of the organic chloride feed.

(4) The caustic treating step for chloride removal from the isobutane product in prior art isomerization can be eliminated in the integrated ionic liquid alkylation-butane isomerization process, since the ionic liquid alkylation reactor can readily accept the HCl containing isobutane stream from the distillation unit as-is. This elimination of the isobutane product treating step further simplifies the integrated ionic liquid alkylation-isomerization process.

By integrating n-butane isomerization with ionic liquid catalyzed alkylation according to embodiments of the present invention, a substantially simplified and less costly, yet more efficient, alkylation process is provided.

Feedstocks for Ionic Liquid Catalyzed Alkylation

In an embodiment, feedstocks for integrated ionic liquid catalyzed alkylation and n-butane isomerization processes may comprise various hydrocarbon streams in a petroleum refinery, a gas-to-liquid conversion plant, a coal-to-liquid conversion plant, or in naphtha crackers, middle distillate crackers, or wax crackers, including FCC off-gas, FCC light naphtha, coker off-gas, coker naphtha, hydrocracker naphtha, and the like.

Examples of olefin containing streams include FCC off-gas, coker gas, olefin metathesis unit off-gas, polyolefin gasoline unit off-gas, methanol to olefin unit off-gas, FCC light naphtha, coker light naphtha, Fischer-Tropsch unit condensate, and cracked naphtha. Some olefin containing streams may contain two or more olefins selected from ethylene, propylene, butylenes, pentenes, and up to $C_{10}$ olefins, i.e., an olefin containing stream used as a feed to the alkylation reactor during an integrated ionic liquid catalyzed alkylation-isomerization process may comprise at least one $C_2$-$C_{10}$ olefin. Such olefin containing streams are further described, for example, in U.S. Pat. No. 7,572,943, the disclosure of which is incorporated by reference herein in its entirety.

Examples of isoparaffin containing streams include, but are not limited to, FCC naphtha, hydrocracker naphtha, coker naphtha, Fisher-Tropsch unit condensate, and cracked naphtha. Such streams may comprise at least one $C_4$-$C_{10}$ isoparaffin. In an embodiment, such streams may comprise a mixture of two or more isoparaffins. In a sub-embodiment, an isoparaffin feed to the alkylation reactor during an integrated ionic liquid catalyzed alkylation-isomerization process may comprise isobutane, which may be obtained, for example, from a hydrocracking unit or may be purchased.

In an embodiment, olefins and isoparaffins fed to the ionic liquid alkylation reactor may participate in ionic liquid catalyzed isoparaffin-olefin alkylation reactions. In another embodiment, olefins in the feed(s) may undergo oligomerization when contacted with an ionic liquid catalyst in a hydrocarbon conversion reactor. Ionic liquid catalyzed olefin oligomerization may take place under the same or similar conditions as ionic liquid catalyzed olefin-isoparaffin alkylation. Ionic liquid catalyzed olefin oligomerization and olefin-isoparaffin alkylation are disclosed, for example, in commonly assigned U.S. Pat. Nos. 7,572,943 and 7,576,252, the disclosures of which are incorporated by reference herein in their entirety.

Ionic Liquid Catalysts

Ionic liquids are generally organic salts with melting points below 100° C. and often below room temperature. They may find applications in various chemical reactions, solvent processes, and electrochemistry. The use of chloroaluminate ionic liquids as alkylation catalysts in petroleum refining has been described, for example, in commonly assigned U.S. Pat. Nos. 7,531,707, 7,569,740, and 7,732,654, the disclosure of each of which is incorporated by reference herein in its entirety.

Most ionic liquids are prepared from organic cations and inorganic or organic anions. Cations include, but are not limited to, ammonium, phosphonium and sulphonium. Anions include, but are not limited to, $BE_4^-$, $PF_6^-$, haloaluminates such as $Al_2Cl_7^-$ and $Al_2Br_7^-$, $[(CF_3SO_2)_2N]^-$, alkyl sulfates ($RSO_3^-$), and carboxylates ($RCO_2^-$). Ionic liquids for acid catalysis may include those derived from ammonium halides and Lewis acids, such as $AlCl_3$, $TiCl_4$, $SnCl_4$, and $FeCl_3$. Chloroaluminate ionic liquids are perhaps the most commonly used ionic liquid catalyst systems for acid catalyzed reactions.

Exemplary ionic liquids for use as catalysts in ionic liquid catalyzed alkylation reactions may comprise at least one compound of the general formulas A and B:

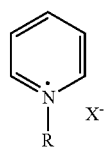

A

B wherein R is H, methyl, ethyl, propyl, butyl, pentyl or hexyl, each of $R_1$ and $R_2$ is H, methyl, ethyl, propyl, butyl, pentyl or hexyl, wherein $R_1$ and $R_2$ may or may not be the same, and X is a chloroaluminate.

Non-limiting examples of chloroaluminate ionic liquid catalysts that may be used in alkylation processes according to embodiments of the instant invention include those comprising 1-butyl-4-methyl-pyridinium chloroaluminate, 1-butyl-3-methyl-imidazolium chloroaluminate, 1-H-pyridinium chloroaluminate, N-butylpyridinium chloroaluminate, and mixtures thereof.

Integrated Butane Isomerization and Ionic Liquid Catalyzed Alkylation Processes

Figure 2:
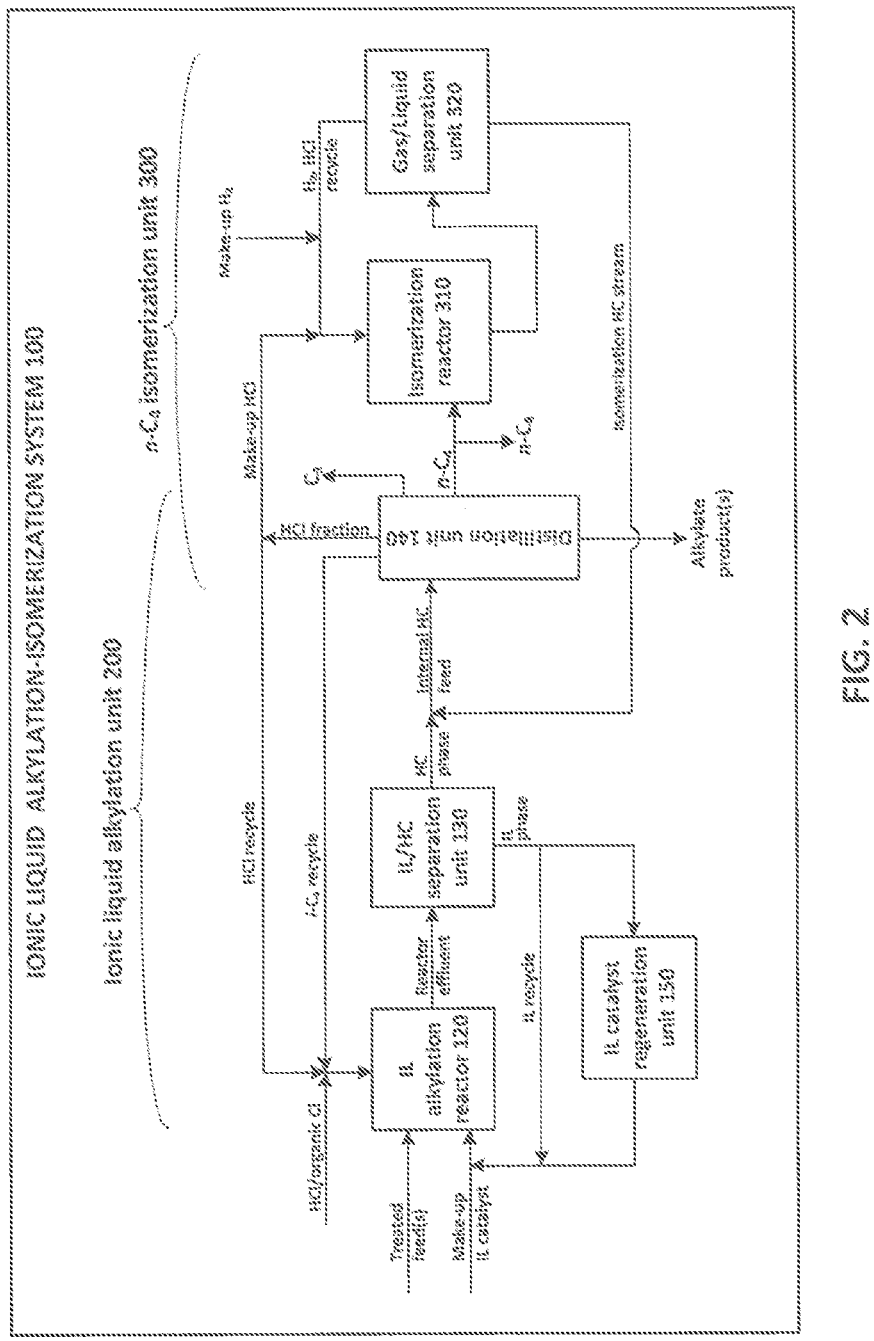
FIG. 2 schematically represents a system and scheme for an integrated ionic liquid alkylation and n-butane isomerization process, according to an embodiment of the present invention.
Figure 3:
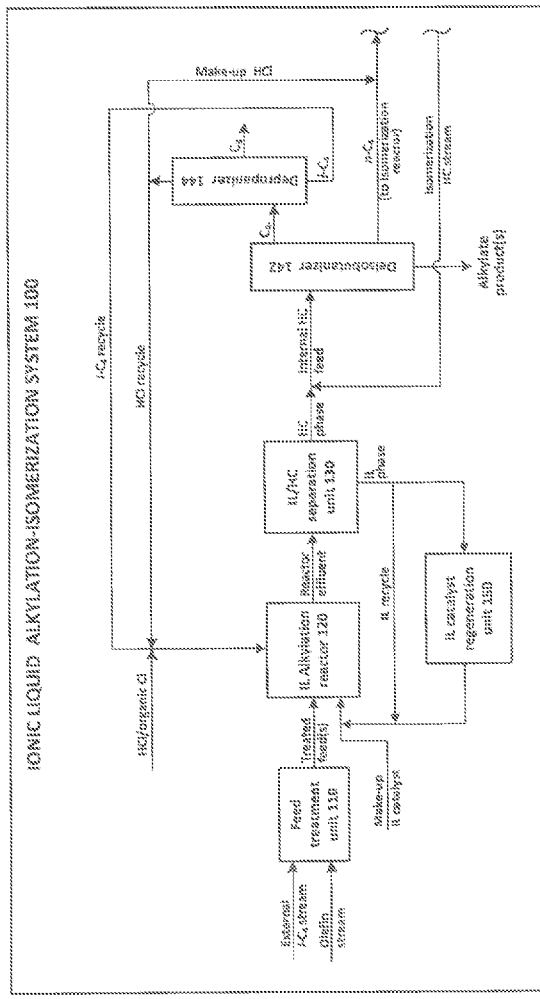
FIG. 3 schematically represents a system and scheme for an integrated ionic liquid alkylation and n-butane isomerization process, according to another embodiment of the present invention.

An integrated ionic liquid alkylation and n-butane isomerization process, according to an embodiment of the present invention will now be described with reference to FIGS. 2 and 3. FIG. 2 schematically represents a system and scheme for an integrated ionic liquid alkylation and n-butane isomerization process, according to an embodiment of the present invention. FIG. 3 schematically represents a system and scheme for an integrated ionic liquid alkylation and n-butane isomerization process, according to another embodiment.

With reference to FIG. 2, an ionic liquid alkylation-isomerization system 100 may comprise an ionic liquid alkylation unit 200, and an n-butane isomerization unit 300 integrated with ionic liquid alkylation unit 200. In an embodiment, integrated ionic liquid alkylation-isomerization processes may involve ionic liquid catalyst catalyzed alkylation and Pt- or Pd-alumina catalyst catalyzed n-butane isomerization. In an embodiment, ionic liquid alkylation and butane isomerization processes may both use (e.g., share) the same distillation unit.

With further reference to FIG. 2, ionic liquid alkylation unit 200 may comprise an ionic liquid alkylation reactor 120, an ionic liquid/hydrocarbon separation unit 130, a distillation unit 140, and an ionic liquid catalyst regeneration unit 150. During ionic liquid catalyzed alkylation, an ionic liquid catalyst and one or more hydrocarbons may be introduced into ionic liquid alkylation reactor 120.

In an embodiment, the hydrocarbon streams fed to ionic liquid alkylation reactor 120 may comprise at least one olefin containing stream and at least one isoparaffin containing stream. Such olefin containing- and isoparaffin containing streams may be treated by a feed treatment unit 110 (see, e.g., FIG. 3), and such streams may be fed from feed treatment unit 110 to ionic liquid alkylation reactor 120. Feedstocks and ionic liquid catalysts that may be suitable for integrated ionic liquid alkylation-isomerization processes are described, for example, hereinabove.

Ionic liquid catalyzed alkylation may involve contacting at least one isoparaffin and at least one olefin with the ionic liquid catalyst, e.g., in ionic liquid alkylation reactor 120, under ionic liquid alkylation conditions. Ionic liquid alkylation reactor 120 may also be referred to herein as an ionic liquid alkylation zone. Exemplary reaction conditions for ionic liquid alkylation according to embodiments of the present invention are described hereinbelow.

Butane isomerization unit 300 may comprise distillation unit 140, an isomerization reactor 310, and a gas/liquid separation unit 320. In an embodiment, at least a portion (e.g., one or more distillation columns) of distillation unit 140 may be common to both ionic liquid alkylation unit 200 and butane isomerization unit 300. Isomerization reactor 310 may also be referred to herein as an isomerization zone. In an embodiment, n-butane isomerization using system 100 may involve contacting an n-butane containing fraction with an isomerization catalyst in isomerization reactor 310 under butane isomerization conditions, wherein at least a portion of the n-butane in the n-butane containing fraction may be isomerized to provide isobutane.

In an embodiment, the ionic liquid alkylation conditions may include the presence of chloride. As a non-limiting example, a co-catalyst such as anhydrous HCl, and/or a catalyst promoter such as an alkyl chloride, may be fed to ionic liquid alkylation reactor 120. Such co-catalyst and/or catalyst promoter may be fed or added to ionic liquid alkylation reactor 120 from an external source to compensate for the loss of chloride by the process. By "external source" is meant a source other than a stream that is derived from or recycled within an integrated ionic liquid alkylation-butane isomerization process.

The conditions for n-butane isomerization may also include the presence of chloride. In an embodiment, the chloride that was added to the ionic liquid alkylation zone may be passed or fed from the ionic liquid alkylation zone to the isomerization zone, e.g., via distillation unit 140, to provide the chloride used for n-butane isomerization. In an embodiment, the chloride present in the isomerization zone may consist essentially of the chloride added to the ionic liquid alkylation zone.

During integrated ionic liquid alkylation-isomerization processes according to embodiments of the present invention, an alkylation reactor effluent of ionic liquid alkylation reactor 120 may be fed to ionic liquid/hydrocarbon separation unit 130 for separating an alkylation hydrocarbon phase from the alkylation reactor effluent. In an embodiment, an ionic liquid phase may also be separated from the alkylation reactor effluent for recycling to ionic liquid alkylation reactor 120.

Integrated ionic liquid alkylation-isomerization processes may further involve feeding at least one hydrocarbon stream to distillation unit 140. The at least one hydrocarbon stream fed to distillation unit 140 may be referred to herein as an internal hydrocarbon feed (see, e.g., FIG. 2). The internal hydrocarbon feed may comprise a mixture of hydrocarbon streams derived from within the integrated ionic liquid alkylation-isomerization process. In an embodiment, the internal hydrocarbon feed may comprise at least a portion of the alkylation hydrocarbon phase from ionic liquid/hydrocarbon separation unit 130. The internal hydrocarbon feed may be fractionated, e.g., via distillation unit 140, to provide the n-butane containing fraction, a $C_3$ fraction, and at least one alkylate product.

The n-butane containing fraction may be fed from distillation unit 140 to isomerization reactor 310. Integrated ionic liquid alkylation-isomerization processes may involve isomerizing the n-butane in the n-butane containing fraction to provide isobutane. Such n-butane isomerization may involve contacting the n-butane containing fraction with an isomerization catalyst in isomerization reactor 310 under conditions suitable for isomerizing the n-butane to isobutane. Such conditions may be referred to herein as butane isomerization conditions. An isomerization catalyst for use in embodiments of integrated ionic liquid alkylation-isomerization processes may comprise, for example, a Pt-alumina catalyst, a Pd-alumina catalyst, or a Pt/Pd-alumina catalyst, or combinations thereof. These noble metal catalysts may typically be treated with anhydrous chloride, e.g., to enhance their catalytic activity.

An isomerization reactor effluent of isomerization reactor 310 may be separated, e.g., by gas/liquid separation unit 320, to provide a gas phase and an isomerization hydrocarbon stream. The gas phase or gaseous fraction may comprise molecular hydrogen and HCl. In an embodiment, the molecular hydrogen and HCl may be recycled from gas/liquid separation unit 320 to isomerization reactor 310.

In an embodiment, the isomerization hydrocarbon stream may be fed, together with the alkylation hydrocarbon phase, to distillation unit 140 to form the internal hydrocarbon feed to distillation unit 140. For example, the internal hydrocarbon feed that is fed to distillation unit 140 may comprise the alkylation hydrocarbon phase and the isomerization hydrocarbon stream. The isomerization hydrocarbon stream may comprise isobutane, a small amount of $C_{5+}$ hydrocarbons, and unreacted n-butane. In an embodiment, the isomerization hydrocarbon stream may comprise predominantly isobutane.

The internal hydrocarbon feed may be fractionated via distillation unit 140 to further provide an isobutane containing fraction, and the isobutane containing fraction may be recycled from distillation unit 140 to ionic liquid alkylation reactor 120 to provide additional isobutane reactant for participation in ionic liquid catalyzed isoparaffin-olefin alkylation reactions.

The alkylation hydrocarbon phase of the ionic liquid alkylation reactor effluent may comprise alkylate. The alkylation hydrocarbon phase may be fed to distillation unit 140, e.g., as a component of the internal hydrocarbon feed (see, for example, FIG. 2). The alkylation hydrocarbon phase may be fractionated via distillation unit 140 to provide at least one alkylate product. The at least one alkylate product may comprise, for example, alkylate gasoline, diesel fuel, jet fuel, base oil, and combinations thereof.

An HCl containing fraction may be separated or recovered from the internal hydrocarbon feed, e.g., via distillation unit 140, for recycling to ionic liquid alkylation reactor 120 and/or isomerization reactor 310. In an embodiment, at least a portion of the HCl containing fraction may be recycled to at least one of ionic liquid alkylation reactor 120 and isomerization reactor 310. In another embodiment, a first portion of the HCl containing fraction may be recycled to ionic liquid alkylation reactor 120, and a second portion of the HCl containing fraction may be recycled to isomerization reactor 310. In an embodiment, the HCl containing fraction may comprise an HCl-rich $C_{3-}$ fraction.

Distillation unit 140 may comprise a plurality of distillation columns. As a non-limiting example, in the embodiment of FIG. 3 the distillation unit may comprise a deisobutanizer 142 and a depropanizer 144. In an embodiment an internal hydrocarbon feed, which comprises the alkylation hydrocarbon phase from ionic liquid alkylation reactor 120 and the isomerization hydrocarbon stream from gas/liquid separation unit 320, may be fed to deisobutanizer 142. (Gas/liquid separation unit 320 and isomerization reactor 310 (see, e.g., FIG. 2) are not shown in FIG. 3 for the sake of clarity.)

With further reference to FIG. 3, the internal hydrocarbon feed may be fractionated via deisobutanizer 142 to provide the n-butane containing fraction and a $C_{4-}$ fraction. The n-butane containing fraction may be fed from deisobutanizer 142 to the isomerization zone or reactor 310, and the isomerization reactor effluent of isomerization reactor 310 may be separated, e.g., by gas/liquid separation unit 320, to provide an isomerization hydrocarbon stream, substantially as described hereinabove.

The C$_{4-}$ fraction from deisobutanizer 142 may be fed to depropanizer 144. The C$_{4-}$ fraction may be fractionated, via depropanizer 144, to provide an isobutane containing fraction, a propane product, and an HCl containing C$_{3-}$ fraction. At least a portion of the HCl containing fraction may be recycled to ionic liquid alkylation reactor 120, e.g., substantially as described hereinabove. Another portion of the HCl containing fraction may be sent to isomerization reactor 310 to make-up the chloride lost in the process. The isobutane containing fraction may be recycled from depropanizer 144 to ionic liquid alkylation reactor 120.

In an embodiment, the isobutane containing fraction may comprise chloride at a concentration in the range from 10 ppm to 10,000 ppm. These chloride levels may be generally suitable or acceptable for feeds to ionic liquid alkylation reactor 120 for conducting ionic liquid catalyzed alkylation reactions. Accordingly, the isobutane containing fraction may be recycled from depropanizer 144 to the ionic liquid alkylation zone in the absence of a chloride removal step.

In alternative configurations (not shown), distillation unit 140 may comprise distillation columns configured other than as shown in FIG. 3. Distillation column configurations may vary, for example, depending on the product volume demands or existing refinery distillation capacity.

In an embodiment, the ionic liquid and hydrocarbons introduced into ionic liquid alkylation reactor 120 may comprise an ionic liquid/hydrocarbon mixture. In an embodiment, the ionic liquid catalyst may comprise a chloroaluminate ionic liquid, such as a compound of the general formulas A and B, supra. The hydrocarbon stream(s) fed to ionic liquid alkylation reactor 120 may be treated via feed treatment unit 110. In an embodiment, the treated hydrocarbon streams may comprise at least one C$_4$-C$_{10}$ isoparaffin and at least one C$_2$-C$_{10}$ olefin. Treatment of the hydrocarbon stream(s) via feed treatment unit 110 may include feed drying, and the removal of dienes, nitrogen and sulfur, as well as the hydroisomerization of olefins in olefin feeds.

In an embodiment, at least a portion of the ionic liquid phase may be recycled from ionic liquid/hydrocarbon separation unit 130 to ionic liquid alkylation reactor 120. With continued operation of system 100, the ionic liquid catalyst may become at least partially deactivated. In order to maintain catalytic activity of the ionic liquid, at least a portion of the ionic liquid phase from ionic liquid/hydrocarbon separation unit 130 may be fed to ionic liquid catalyst regeneration unit 150 for regeneration of the ionic liquid catalyst. Thereafter, the regenerated ionic liquid catalyst may be recycled to ionic liquid alkylation reactor 120. The regeneration of ionic liquid catalysts is disclosed, for example, in commonly assigned U.S. Pat. Nos. 7,674,739, 7,955,999 and 7,956,002, the disclosure of each of which is incorporated by reference herein in its entirety.

Reaction Conditions for Integrated Ionic Liquid Alkylation-Butane Isomerization Processes The ionic liquid alkylation reaction temperature may be generally in the range from about −40° C. to +250° C. (−40° F. to +482° F.), typically from about −20° C. to +100° C. (−4° F. to +212° F.), and often from about +4° C. to +60° C. (+40° F. to +140° F.). The ionic liquid alkylation reactor pressure may be in the range from atmospheric pressure to about 8000 kPa. Typically, the ionic liquid alkylation reactor pressure is sufficient to keep the reactants in the liquid phase.

Residence time of reactants in the ionic liquid alkylation reactor may generally be in the range from a few seconds to hours, and usually from about 0.5 min to 60 min. A hydrocarbon stream introduced into the ionic liquid alkylation reactor may have an isoparaffin:olefin molar ratio generally in the range from about 1-100, more typically from about 2-50, and often from about 2-20.

The volume of ionic liquid catalyst in the ionic liquid alkylation reactor may be generally in the range from about 1 to 70 vol %, and usually from about 4 to 50 vol %. The ionic liquid alkylation reactor conditions may be adjusted to optimize process performance for a particular process or targeted product(s).

Reaction conditions for n-butane isomerization may generally include a temperature in the range from about 50° C. to 200° C. (122° F. to 392° F.), a pressure in the range from atmospheric pressure to about 16,000 kPa, an LHSV of n-butane feed per volume of isomerization catalyst in the range from 1 to about 10 hr$^{-1}$, and a hydrogen to n-butane feed molar ratio in the range from 10 to about 1,000.

Numerous variations on the present invention are possible in light of the teachings described herein. It is therefore understood that within the scope of the following claims, the invention may be practiced otherwise than as specifically described or exemplified herein.

What is claimed is:

1. An integrated ionic liquid alkylation and n-butane isomerization process, comprising:
   a) contacting at least one isoparaffin and at least one olefin with an ionic liquid catalyst in an ionic liquid alkylation zone under ionic liquid alkylation conditions;
   b) separating an alkylation hydrocarbon phase from an alkylation reactor effluent of the ionic liquid alkylation zone;
   c) fractionating, via a distillation unit, an internal hydrocarbon feed to provide an n-butane containing fraction, wherein the internal hydrocarbon feed comprises the alkylation hydrocarbon phase;
   d) contacting the n-butane containing fraction with an isomerization catalyst in an isomerization zone under butane isomerization conditions to provide an isomerization reactor effluent;
   e) via a gas/liquid separation unit, separating the isomerization reactor effluent to provide an isomerization hydrocarbon stream and a gaseous fraction comprising molecular hydrogen and HCl; and
   f) recycling the molecular hydrogen and HCl of the gaseous fraction from the gas/liquid separation unit to the isomerization zone.

2. The process according to claim 1, wherein the internal hydrocarbon feed further comprises the isomerization hydrocarbon stream, and the isomerization hydrocarbon stream comprises isobutane, C$_{5+}$ hydrocarbons, and n-butane.

3. The process according to claim 1, further comprising:
   g) fractionating, via the distillation unit, the internal hydrocarbon feed to further provide an isobutane containing fraction; and
   h) recycling the isobutane containing fraction to the ionic liquid alkylation zone.

4. The process according to claim 3, wherein the distillation unit comprises a deisobutanizer, and
   step c) comprises fractionating, via the deisobutanizer, the internal hydrocarbon feed to provide the n-butane containing fraction and a C$_{4-}$ fraction.

5. The process according to claim 4, wherein the distillation unit further comprises a depropanizer, and the process further comprises:
   i) fractionating, via the depropanizer, the C$_{4-}$ fraction to provide the isobutane containing fraction.

6. The process according to claim 2, further comprising:
j) separating an HCl containing fraction from the internal hydrocarbon feed; and
k) recycling at least a portion of the HCl containing fraction to the ionic liquid alkylation zone.

7. The process according to claim 2, further comprising:
l) separating an HCl containing fraction from the internal hydrocarbon feed; and
m) recycling at least a portion of the HCl containing fraction to the isomerization zone.

8. The process according to claim 1, wherein:
the at least one isoparaffin comprises at least one $C_4$-$C_{10}$ isoparaffin,
the at least one olefin comprises at least one $C_2$-$C_{10}$ olefin, and
the ionic liquid alkylation conditions comprise a reaction temperature in the range from about −20° C. to 100° C., a reactor pressure in the range from atmospheric pressure to 8000 kPa, and an isoparaffin:olefin molar ratio in the range from about 2-50.

9. The process according to claim 1, wherein the ionic liquid catalyst comprises at least one compound of the general formulas A and B:

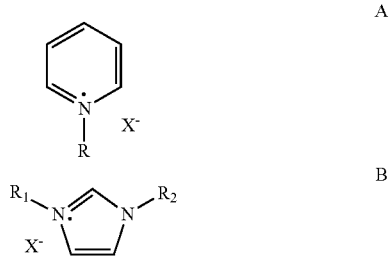

wherein R is H, methyl, ethyl, propyl, butyl, pentyl or hexyl; each of $R_1$ and $R_2$ is H, methyl, ethyl, propyl, butyl, pentyl or hexyl, wherein $R_1$ and $R_2$ may or may not be the same; and X is a chloroaluminate.

10. The process according to claim 1, wherein the alkylation hydrocarbon phase comprises at least one alkylate product, and the process further comprises:
n) separating, via the distillation unit, the at least one alkylate product, wherein the at least one alkylate product is selected from the group consisting of alkylate gasoline, diesel fuel, jet fuel, base oil, and combinations thereof.

11. An integrated ionic liquid alkylation-butane isomerization process, comprising:
a) contacting at least one isoparaffin and at least one olefin with an ionic liquid catalyst in an ionic liquid alkylation zone under ionic liquid alkylation conditions;
b) separating an alkylation hydrocarbon phase from an alkylation reactor effluent of the ionic liquid alkylation zone;
c) fractionating, via a distillation unit, an internal hydrocarbon feed to provide an n-butane containing fraction, wherein the internal hydrocarbon feed comprises the alkylation hydrocarbon phase;
d) contacting the n-butane containing fraction with an isomerization catalyst in an isomerization zone under butane isomerization conditions;
e) via a gas/liquid separation unit, separating an isomerization reactor effluent of the isomerization zone to provide an isomerization hydrocarbon stream and a gaseous fraction comprising molecular hydrogen and HCl, wherein the isomerization hydrocarbon stream comprises isobutane, and the internal hydrocarbon feed further comprises the isomerization hydrocarbon stream;
f) recycling the molecular hydrogen and HCl of the gaseous fraction from the gas/liquid separation unit to the isomerization zone;
g) fractionating, via the distillation unit, the internal hydrocarbon feed to further provide an isobutane containing fraction; and
h) recycling the isobutane containing fraction to the ionic liquid alkylation zone.

12. The process according to claim 11, wherein the distillation unit comprises a deisobutanizer and a depropanizer, step c) comprises fractionating, via the deisobutanizer, the internal hydrocarbon feed to provide the n-butane containing fraction, and step g) comprises:
i) fractionating, via the deisobutanizer, the internal hydrocarbon feed to provide a $C_{4-}$ fraction; and
j) fractionating, via the depropanizer, the $C_{4-}$ fraction to provide the isobutane containing fraction.

13. The process according to claim 12, further comprising:
k) separating, via the depropanizer, an HCl containing fraction from the $C_{4-}$ fraction; and
l) recycling the HCl containing fraction from the depropanizer to at least one of the ionic liquid alkylation zone and the isomerization zone.

14. The process according to claim 11, wherein the butane isomerization conditions include the presence of chloride, the chloride is added to the ionic liquid alkylation zone, and the chloride is fed from the ionic liquid alkylation zone to the isomerization zone via the distillation unit.

15. The process according to claim 11, wherein the isomerization hydrocarbon stream comprises predominantly isobutane.

16. The process according to claim 1, further comprising: prior to step a), drying the at least one isoparaffin and the at least one olefin via a feed treatment unit.

17. An integrated ionic liquid alkylation and n-butane isomerization process, comprising:
a) separating, via a gas/liquid separation unit, an isomerization zone effluent to provide:
 I) a gaseous fraction comprising molecular hydrogen and HCl, and
 II) an isomerization hydrocarbon stream;
b) recycling the gaseous fraction from the gas/liquid separation unit to the isomerization zone;
c) combining the isomerization hydrocarbon stream with an alkylation hydrocarbon phase from an ionic liquid alkylation zone to provide an internal hydrocarbon feed;
d) feeding the internal hydrocarbon feed to a deisobutanizer of a distillation unit;
e) fractionating, via the deisobutanizer, the internal hydrocarbon feed to provide an n-butane containing fraction and a $C_{4-}$ fraction;
f) feeding the $C_{4-}$ fraction from the deisobutanizer to a depropanizer of the distillation unit;
g) fractionating, via the depropanizer, the $C_{4-}$ fraction to provide an isobutane containing fraction; and
h) feeding the isobutane containing fraction from the depropanizer to the ionic liquid alkylation zone.

18. The process according to claim 17, further comprising:
i) feeding the n-butane containing fraction from the deisobutanizer to the isomerization zone; and
j) contacting the n-butane containing fraction with an isomerization catalyst in the isomerization zone under butane isomerization conditions to provide the isomerization zone effluent.

19. The process according to claim 17, further comprising:
k) contacting at least one isoparaffin and at least one olefin with an ionic liquid catalyst in the ionic liquid alkylation zone under ionic liquid alkylation conditions to provide an ionic liquid alkylation zone effluent; and
l) separating, via an ionic liquid/hydrocarbon separation unit, the ionic liquid alkylation zone effluent to provide the alkylation hydrocarbon phase and an ionic liquid phase.

20. The process according to claim 17, wherein the alkylation hydrocarbon phase comprises at least one alkylate product, and the process further comprises:
m) fractionating, via the deisobutanizer, the alkylation hydrocarbon phase to provide the at least one alkylate product.

* * * * *